United States Patent [19]

Nguyen Thanh et al.

[11] Patent Number: 6,054,409

[45] Date of Patent: *Apr. 25, 2000

[54] SELECTIVE HYDROGENATION CATALYST AND A PROCESS USING THAT CATALYST

[75] Inventors: Canh Nguyen Thanh, La Celle Saint Cloud; Blaise Didillon; Patrick Sarrazin, both of Rueil Malmaison; Charles Cameron, Paris, all of France

[73] Assignee: Institut Francais du Petrole, Rueil-Malmaison Cedex, France

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/770,426

[22] Filed: Dec. 20, 1996

Related U.S. Application Data

[63] Continuation-in-part of application No. 08/466,685, Jun. 6, 1995, Pat. No. 5,648,576.

[30] Foreign Application Priority Data

Dec. 22, 1995 [FR] France .................................. 95 15340

[51] Int. Cl.[7] .............................. B01J 23/58; B01J 23/44; C07C 5/03; C07C 5/08
[52] U.S. Cl. ........................ 502/330; 502/328; 502/333; 585/259; 585/260
[58] Field of Search ..................................... 502/330, 260, 502/259, 333, 439, 230, 325, 328, 527; 585/260

[56] References Cited

U.S. PATENT DOCUMENTS

| | | | |
|---|---|---|---|
| 3,651,167 | 3/1972 | de Rosset | 260/681.5 |
| 4,484,015 | 11/1984 | Johnson et al. | 585/259 |
| 4,547,600 | 10/1985 | Cosyns et al. | 585/259 |
| 5,004,859 | 4/1991 | Schmidt et al. | 585/741 |
| 5,475,173 | 12/1995 | Cheung et al. | 585/259 |
| 5,583,274 | 12/1996 | Cheung et al. | 585/259 |
| 5,587,348 | 12/1996 | Brown et al. | 502/230 |
| 5,648,576 | 7/1997 | Than et al. | 585/260 |

FOREIGN PATENT DOCUMENTS

| | | |
|---|---|---|
| 0 064 301 | 11/1982 | European Pat. Off. . |
| 0 686 615 | 12/1995 | European Pat. Off. . |
| 4-108540 | 9/1992 | Japan . |

*Primary Examiner*—Steven Bos
*Attorney, Agent, or Firm*—Millen, White, Zelano & Branigan, P.C.

[57] ABSTRACT

A catalyst is described for selective gas phase hydrogenation of acetylenic compounds containing 2 or 3 carbon atoms to the corresponding ethylenic compounds. The catalyst, in the form of spherules or extrudates, comprises palladium, at least one metal from group IB, optionally at least one alkali or alkaline-earth metal, and alumina, in which at least 80% of the palladium and at least 80% of the element from group IB are present in a volume at the periphery of the catalyst defined between a spherical or cylindrical surface with radius $r_1$ corresponding to the average radius of the spherules or extrudates of the catalyst and a spherical or cylindrical surface with radius $r_2$ at least equal to 0.8 $r_1$, the catalyst having a group IB metal/palladium ratio of 0.4 to 3 by weight. Further, it is advantageous for this catalyst that at least 30% of the metal particles contain both palladium and silver.

27 Claims, 1 Drawing Sheet

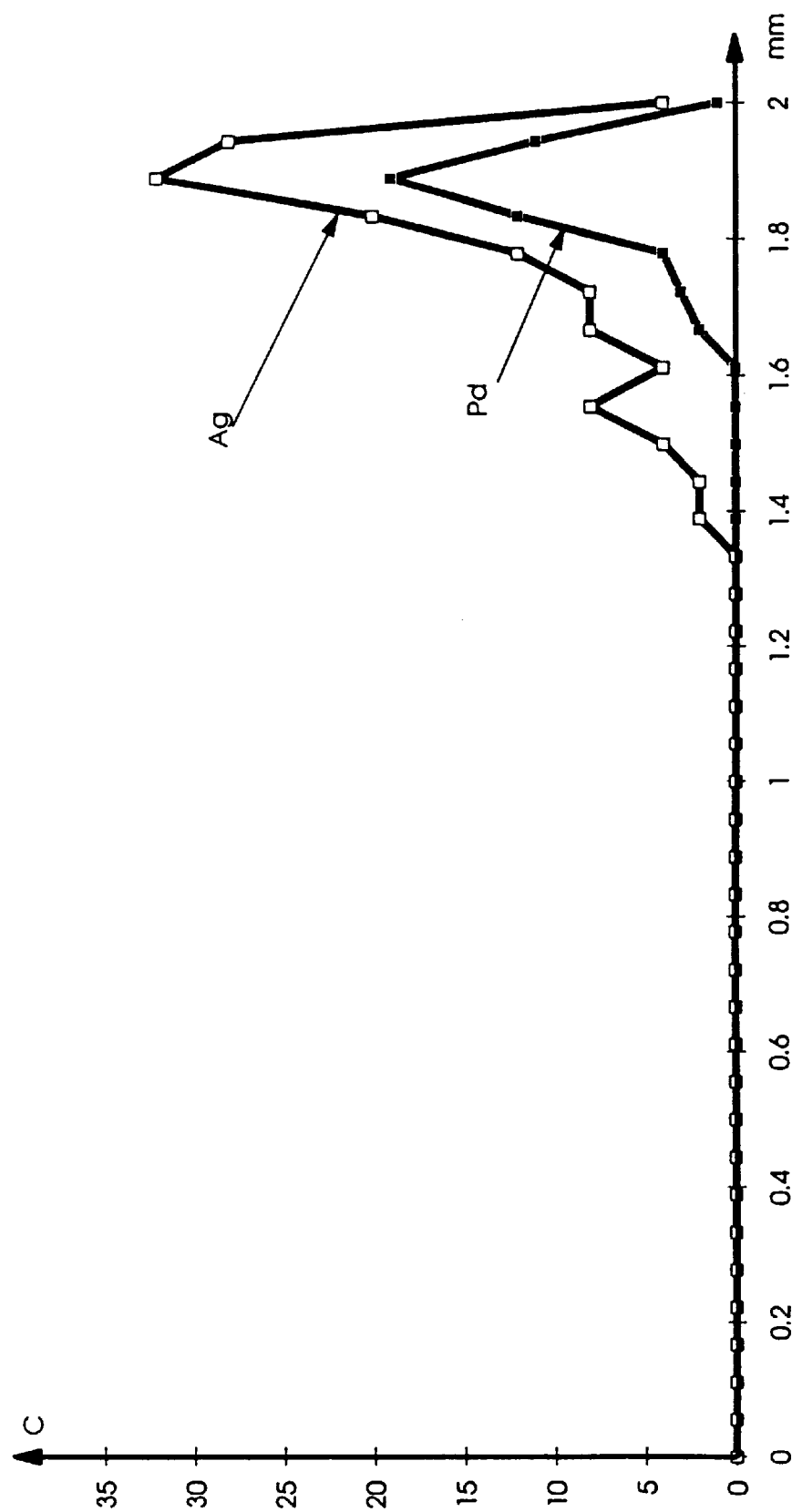

SELECTIVE HYDROGENATION CATALYST AND A PROCESS USING THAT CATALYST

CROSS REFERENCE TO RELATED APPLICATION

This application is a continuation-in-part of application Ser. No. 08/466,685 filed Jun. 6, 1995, now U.S. Pat. No. 5,648,576, issued Jul. 15, 1997, of which priority is claimed of corresponding French applications 94/07044 and 97/07045 filed Jun. 9, 1994.

BACKGROUND OF THE INVENTION

The invention concerns a novel supported catalyst particularly for use for selective gas phase hydrogenation of acetylenic hydrocarbon containing 2 or 3 carbon atoms to the corresponding ethylenic hydrocarbons. More particularly, it concerns a catalyst for selective hydrogenation of acetylenic compounds such as acetylene or propyne to ethylene or propylene respectively, in the gas phase.

It also concerns a selective hydrogenation process using this catalyst.

Ethylene is a monomer which is used in the preparation of a large number of polymers. It is generally obtained by pyrolysis or steam cracking of hydrocarbons. The ethylene which is produced contains small quantities of acetylene (generally less than 3%) which must be eliminated before use. The amount of acetylene which is generally tolerated in ethylene for use in the manufacture of polymers is generally less than 10 ppm, and usually less than 5 ppm.

One technique for eliminating acetylene in ethylene is to selectively hydrogenate it to ethylene in the presence of a palladium based catalyst supported on a refractory support such as alumina. The problem which is generally encountered with monometallic catalysts (constituted solely by palladium supported on alumina) is that when the operating conditions are such as to allow complete elimination of the acetylene, a portion of the ethylene is also converted to ethane. Further, such monometallic catalysts generally have relatively low stability due to the substantial formation of oligomers which gradually cover the surface of the catalyst under the reaction conditions. This hydrocarbon deposit can, of course, be eliminated by oxidation processes, but in an industrial process it is of advantage to have as long an operational time for the catalyst as possible between any two regeneration steps.

Addition of promoters to the palladium has long been proposed to improve the properties of the catalysts. Such additions can, for example, be silver (U.S. Pat. No. 2,802,889) or iron and silver (U.S. Pat. No. 3,243,387).

Such promoters can also be selected from alkali metals or alkaline-earth metals such as lithium (U.S. Pat. No. 3,325,556), potassium (European application EP-A-0 124 744) or calcium (U.S. Pat. No. 4,329,530).

Whether using monometallic catalysts (based on palladium alone) or promoted catalysts (comprising palladium and at least one other element), the skilled person is aware that when the palladium is concentrated at the surface of the catalyst particles (for example spherules), its catalytic performances are substantially superior to those of a catalyst with an identical formula where the palladium is homogeneously distributed in the catalyst particles. As an example, when using bimetallic palladium-silver formulae, it has been discovered that when the palladium is situated at the periphery of the catalyst spherules and the silver is homogeneously distributed, this improves the properties of the catalyst (U.S. Pat. No. 4,404,124; EP-A-0 064 301 and French patent FR-A-2 597 113), in particular by a reduction in ethane formation and a reduction in oligomerisation product formation.

In addition, Japanese patent application JP-A-04 108540 describes selective liquid phase hydrogenation catalysts for 1–3-butadiene, in which the silver is precipitated and supported at the surface of the palladium. In such catalysts, the support consists of alumina with a relatively high specific surface area and the Ag/Pd ratio is 0.5:1 to 3.0:1 by weight, preferably 0.5:1 to 3.0:1 by weight.

In a prior patent application (FR-A-2 721 018, filed on $9^{th}$ June 1994), a selective gas phase process is described for hydrogenating acetylenic hydrocarbons containing 2 or 3 carbon atoms (acetylene or propyne) to the corresponding ethylenic hydrocarbons (ethylene or propylene) using a catalyst in the form of spherules or extrudates containing palladium, at least one metal from group IB of the periodic classification, and alumina, in which a proportion of at least 80% of the palladium and a proportion of at least 80% of the group IB metal is present in a volume at the periphery of the catalyst delimited by a spherical or cylindrical surface with radius $r_1$ corresponding to the average radius of the catalyst spherules or extrudates and a spherical or cylindrical surface with radius $r_2$ which is at least equal to $0.8\ r_1$. The silver/palladium ratio is in the range 0.05 to 0.4 by weight, preferably in the range 0.05 to 0.25 by weight.

More particularly, the palladium content is in the range 0.01% to 0.05% by weight of the catalyst. The group IB element, normally silver, is present in an amount in the range 0.001% to 0.02% by weight of catalyst.

For the industrial application envisaged, the catalyst performances must vary as little as possible over time. In fact, a catalyst for which acetylene is firstly totally converted but in which the acetylene would appear very rapidly at the reactor outlet at high concentrations, could not be used as it would cause considerable control problems in the industrial unit. This means that one of the selection criteria for the hydrogenation catalyst is its deactivation, which corresponds to the speed at which acetylene appears at the reactor outlet. Such deactivation must be as long as possible.

SUMMARY OF THE INVENTION

We have now discovered that it is possible to reduce the deactivation tendency of acetylene hydrogenation catalysts such as those described by us in French patent application FR-A-2 721 018 filed on $6^{th}$ June 1994.

The invention thus provides a novel catalyst in the form of spherules or substantially cylindrical extrudates which are defined as containing palladium, at least one metal from group IB of the periodic classification, and alumina, the ratio of group IB metal to palladium being 0.4 to 3, preferably 0.5 to 3, more preferably 0.5 to 2.5; a proportion of at least 80% of the palladium and a proportion of at least 80% of the group IB metal being present in a volume at the periphery of the catalyst delimited by a spherical or cylindrical surface with radius $r_1$ corresponding to the average radius of the catalyst spherules or extrudates and a spherical or cylindrical surface with radius $r_2$ which is at least equal to $0.8\ r_1$.

When the catalysts are in the form of spherules or extrudates, $r_1$ and $r_2$ can be represented as follows:

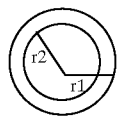

Further, it is advantageous that at least 30%, preferably at least 40%, more preferably at least 50%, of the metallic particles, analysed by electron microscopy, contain both palladium and silver.

More particularly, the palladium content is in the range 0.01% to 0.5% by weight of catalyst. The group IB element is normally silver in an amount which is in the range 0.001% to 0.1% by weight.

The support is an alumina, more particularly an alumina which is essentially constituted by alpha alumina. It is generally used in the form of spherules or extrudates with diameters-which are generally in the range 2 mm to 4 mm. The alumina generally has the following characteristics: a specific surface area which is in the range 5 $m^2$/g to 60 $m^2$/g, preferably 5 $m^2$/g to 15 $m^2$/g; a pore volume of 0.3 $cm^3$/g to 0.95 $cm^3$/g and a pore diameter of over 100 Å. These diverse characteristics are determined using analytical techniques which are known to the skilled person.

Palladium can be introduced using techniques which are known to the skilled person for producing a palladium distribution at the surface of the support spherules or extrudates, which corresponds to the criteria described above. Correct distribution of the palladium can be verified using conventional techniques such as a Castaing microprobe. The palladium can, for example, be introduced by impregnation using an aqueous or organic solution of a palladium precursor. The precursor can, for example, be an inorganic compound such as palladium chloride, palladium nitrate, palladium tetrammine dihydroxide, palladium tetrammine chloride, or an organometallic compound such as palladium bis π allyl or palladium bis-acetylacetonate.

The group IB element, in particular silver, is introduced in such a manner that it remains concentrated at the periphery of the spherules or extrudates of the support. Analysis of the silver content after controlled abrasion of catalyst spherules ascertains the correct distribution of the silver in the catalyst spherules or extrudates. When the silver content is sufficient, correct distribution of the silver can be verified by Castaing microprobe. Silver nitrate is generally used as the precursor. Silver acetate, silver citrate, silver chloride, and silver oxalate can also be used. The composition of the metal particles can be analysed by electron microscopy.

The catalysts of the invention which can be used in a process for selective gas phase hydrogenation of acetylenic hydrocarbons containing 2 or 3 carbon atoms to the corresponding ethylenic hydrocarbons can also contain at least one alkali or alkaline-earth metal.

In this case, the alkali or alkaline-earth metal content in the catalyst is advantageously selected so that the ratio of alkali or alkaline-earth metal to palladium is in the range 2 to 20, preferably in the range 4 to 15. Preferably, this content is in the range 0.05% to 0.2% by weight of catalyst.

The alkali metal is preferably sodium or potassium. The alkaline-earth metal is preferably magnesium.

The alkali or alkaline-earth metal is introduced using techniques which are known to the skilled person. Precursors which are generally used are nitrates, acetates, chlorides, carbonates and hydroxides.

The palladium and the group IB metal, and optionally the alkali or alkaline-earth metal, can be introduced from a common solution of their precursors or from separate solutions each containing one or two elements. In the latter case, drying, calcining or reduction at temperatures in the range 120° C. to 900° C. can optionally be carried out between two consecutive impregnation steps.

When the palladium and the group IB element (in particular silver) are introduced from different solutions, the preparation techniques which can be used are, for example, those described in U.S. Pat. No. 4,533,779, which use silver chloride as the precursor or U.S. Pat. No. 4,504,593 which uses silver citrate as the precursor.

The catalyst obtained is generally dried at temperatures in the range from ambient temperature to 150° C. The dried catalyst can be used as it is or, more often, it is preferably calcined to decompose the metallic precursor and/or it is reduced before use. Calcining is generally carried out by treating the catalyst in a stream of air at a temperature which is in the range 400° C. to 900° C. Reduction can be carried out by treating the catalyst with a hydrogen-containing gas at a temperature which is in the range from ambient temperature to 500° C.

The hydrogenation process of the invention using the catalysts described above is particularly suitable for hydrogenation of acetylene present in a gas containing ethylene. In order to reach the reaction conditions under which the acetylene is completely eliminated, the molar ratio of hydrogen to acetylene is generally in the range 1 to 2, the reaction temperature is generally in the range 25° C. to 100° C., and the pressure is generally in the range 1 to 5 MPa. The feed flow rate, expressed in litres of gaseous feed per litre of catalyst per hour, is generally in the range 1000 $h^{-1}$ to 10000 $h^{-1}$.

During use, the catalyst deactivates due to deposition of hydrocarbon compounds which gradually cover the active phase. When the catalyst performances are judged to be insufficient, the catalyst can be regenerated. The catalyst is regenerated by controlled combustion of the hydrocarbon species present thereon. Combustion takes place under conditions which are known to the skilled person, generally by slowly heating the catalyst in the presence of a gas containing oxygen at a temperature which is in the range 350° C. to 500° C.

The following non limiting examples illustrate the invention. Examples 4, 5 and 7 are given by way of comparison.

EXAMPLE 1 (in accordance with the invention)

A catalyst in accordance with the invention (catalyst A) was prepared by impregnating 100 g of a support based on alpha alumina with 60 ml of a nitric acid solution containing palladium nitrate and silver nitrate. The support was in the form of spherules with a diameter of 2 mm to 4 mm with a specific surface area of 10 $m^2$/g and a pore volume of 0.6 $cm^3$/g. After impregnation, the catalyst was dried at 120° C. and calcined in air at 750° C. Catalyst A obtained contained 0.025% by weight of palladium and 0.050% by weight of silver the ag:Pd ratio being 2:1. The average distribution of the elements in the catalyst grains is shown in FIG. 1. These analyses show that more than 80% of the silver and almost all of the palladium were concentrated in a volume delimited by a sphere with radius $r_1$=2 mm and a sphere with radius $r_2$ of 1.6 mm. The Ag/Pd weight ratio was 2. Analysis of the catalyst particles by electron microscopy (STEM) showed that 60% of the particles contained both palladium and silver.

EXAMPLE 2 (in accordance with the invention)

A catalyst in accordance with the invention (catalyst B) was prepared by impregnating 100 g of a support based on alpha alumina with 60 ml of a nitric acid solution containing palladium nitrate, sodium nitrate and silver nitrate. The support was in the form of spherules with a diameter of 2 mm to 4 mm with a specific surface area of 10 $m^2/g$ and a pore volume of 0.6 $cm^3/g$. After impregnation, the catalyst was dried at 120° C. and calcined in air at 750° C. Catalyst B obtained contained 0.025% by weight of palladium, 0.05% by weight of sodium and 0.050% by weight of silver. Castaing microprobe analysis showed that the elements were distributed at the periphery of the catalyst spherules. The Ag/pd weight ratio was 2:1. Analysis of the metallic particles of the catalyst by electron microscopy (STEM) showed that 75% of the particles contained both palladium and silver.

EXAMPLE 3 (in accordance with the invention)

A catalyst in accordance with the invention (catalyst C) was prepared by impregnating 100 g of a support based on alpha alumina with 60 ml of a nitric acid solution containing palladium nitrate, sodium nitrate and silver nitrate. The support was in the form of spherules with a diameter of 2 mm to 4 mm with a specific surface area of 10 $m^2/g$ and a pore volume of 0.6 $cm^3/g$. After impregnation, the catalyst was dried at 120° C. and calcined in air at 750° C. Catalyst C obtained contained 0.05% by weight of palladium, 0.05% by weight of sodium and 0.052% by weight of silver. Castaing microprobe analysis showed that the elements were distributed at the periphery of the catalyst spherules. The Ag/Pd weight ratio was 1.04:1. Analysis of the metallic particles of the catalyst by electron microscopy (STEM) showed that 43% of the particles contained both palladium and silver.

EXAMPLE 4 (comparative)

A catalyst (catalyst D) was prepared by impregnating 100 g of a support based on alpha alumina with 60 ml of a nitric acid solution containing palladium nitrate, sodium nitrate and silver nitrate. The support was in the form of spherules with a diameter of 2 mm to 4 mm with a specific surface area of 10 $m^2/g$ and a pore volume of 0.6 $cm^3/g$. After impregnation, the catalyst was dried at 120° C. and calcined in air at 750° C. Catalyst D obtained contained 0.025% by weight of palladium, 0.05% by weight of sodium and 0.0025% by weight of silver. Castaing microprobe analysis showed that the elements were distributed at the periphery of the catalyst spherules. However, the Ag/Pd weight ratio of 0.1:1 was outside the characterising range of the invention. Analysis by electron microscopy (STEM) showed that 35% of the metallic particles contained both palladium and silver.

EXAMPLE 5 (comparative)

A comparative catalyst E was prepared by immersing 100 g of a support in 120 ml of an aqueous silver nitrate solution containing 9 g of silver. The catalyst was stirred for 20 minutes. The supernatant solution was then eliminated. The catalyst was washed, and dried at 120° C. This solid was then impregnated with 60 ml of a solution of nitric acid and palladium nitrate. The catalyst was then dried and calcined in air at 750° C. Catalyst E obtained contained 0.025% by weight of palladium and 0.05% by weight of silver. The Ag/Pd weight ratio was 2, but microprobe analysis showed that the silver was homogeneously distributed in the catalyst grains while the palladium was distributed at its periphery. Analysis of the metallic particles by electron microscopy (STEM) showed that 2% of the analysed particles contained both palladium and silver.

EXAMPLE 6 (in accordance with the invention)

A catalyst in accordance with the invention (catalyst F) was prepared by impregnating 100 g of a support based on alpha alumina with 60 ml of a nitric acid solution containing palladium nitrate, sodium nitrate and silver nitrate. The support was in the form of spherules with a diameter of 2 mm to 4 mm with a specific surface area of 10 $m^2/g$ and a pore volume of 0.6 $cm^3/g$. After impregnation, the catalyst was dried at 120° C. and calcined in air at 750° C. Catalyst F obtained contained 0.025% by weight of palladium, 0.015% by weight of sodium and 0.030% by weight of silver. Castaing microprobe analysis showed that the elements were distributed at the periphery of the catalyst spherules. The Ag/Pd weight ratio was 1.2:1. Analysis of the metallic particles of the catalyst by electron microscopy (STEM) showed that 40% of the particles contained both palladium and silver.

EXAMPLE 7 (comparative)

A catalyst G was prepared by impregnating 100 g of a support with 60 ml of a solution of palladium nitrate dissolved in nitric acid, at ambient temperature. The support was in the form of spherules with a diameter of 2 mm to 4 mm with a specific surface area of 10 $m^2/g$ and a pore volume of 0.6 $cm^3/g$. After impregnation, the catalyst was dried at 120° C. and calcined in air at 750° C. The catalyst was then impregnated with 0.6 $cm^3$ of a silver nitrate solution. The catalyst was then dried and calcined and contained 0.025% by weight of palladium and 0.0500% by weight of silver. Microprobe analysis showed that the palladium and silver were distributed at the periphery of the catalyst spherules. The Ag/Pd ratio was 2. Analysis by electron microscopy (STEM) showed that only 8% of the metallic particles contained both palladium and silver.

EXAMPLE 8

Comparison of the Hydrogenating Properties of Different Catalysts

Catalytic test were carried out on catalysts A, B, C, D, E, F and G to determine their selectivity, stability and deactivation during hydrogenation of the acetylene contained in a feed containing 98% of ethylene and 2% of acetylene.

15 ml of the catalyst to be tested was placed in a vertical steel reactor. The reactor was then placed in an oven to control the temperature. Firstly, the catalyst was reduced in a stream of hydrogen at 150° C. for 2 hours at atmospheric pressure. The temperature was then brought to 50° C., the hydrogen flow rate to 1.5 $h^{-1}$ and the pressure to 2.5 MPa. The feed, composed of 98% of ethylene and 2% of acetylene, was then injected at a volume flow rate which corresponded to a space velocity of 3300 $h^{-1}$. Analysis of the gaseous effluent at the reactor outlet was carried out using gas chromatography. Under these conditions, the stability of the catalyst was defined as the time (in hours) after which acetylene was detected at the reactor outlet. The catalyst selectivity (in %) corresponded to the ethylene content of the feed after total elimination of the acetylene. The catalyst deactivation corresponded to the rate (in mole %/hour) of appearance of ethylene from the time which defined the stability. The results obtained are shown in Table 1.

TABLE 1

Comparison of performances of catalysts A, B, C, D, E, F and G for hydrogenation of acetylene

| Catalyst | Stabilities (h) | Selectivities (%) | Deactivation (mole %/hour) |
|---|---|---|---|
| A (invention) | 45 | 98.7 | 7 |
| B (invention) | 52 | 98.6 | 7 |
| C (invention) | 49 | 98.5 | 10 |
| D (comparative) | 48 | 98.5 | 16 |
| E (comparative) | 15 | 98.3 | 25 |
| F (invention) | 50 | 98.6 | 8 |
| G (comparative) | 4 | 97.9 | 21 |

These results clearly show that when the Ag/Pd ratio is 1.2 (catalyst F), 1.04 (catalyst C) or 2.0 (catalysts A and B), catalyst deactivation is lower than that obtained with catalysts where the Ag/Pd ratio is 0.1 (catalyst D).

When the silver is distributed homogeneously in the catalyst grain (catalyst E), the deactivation rate is higher and the catalyst is less stable than when the silver is distributed at the periphery of the catalyst spherules (catalyst C). Further, when only 8% of the metallic particles contain both silver and palladium (catalyst G), the stability and selectivity are lower and the deactivation is higher than those obtained with a catalyst in which, for example, 60% of the particles contain both palladium and silver (catalyst A).

What we claimed is:

1. A catalyst in the form of spherules or extrudates, comprising palladium and silver, incorporated as metallic particles on an alumina support, at least 30% of said metallic particles containing both palladium and silver, as measured by electron microscopy said alumina support having a specific surface of from 5 to 60 m$^2$/g, the weight ratio of silver to palladium being higher than 0.4:1 to 3:1, a proportion of at least 80% of the palladium and a proportion of at least 80% of silver being present in a volume at the periphery of the catalyst delimited by a spherical or cylindrical surface with radius $r_1$ corresponding to the average radius of the catalyst spheniles or extrudates and a spherical or cylindrical surface with radius $r_2$ corresponding to the average radius of the catalyst spherules or extrudates and a spherical or cylindrical surface with radius $r_2$ which is at least equal to 0.8 $r_1$.

2. A catalyst according to claim 1, wherein at least 50% of the metallic particles contain both palladium and silver.

3. A catalyst according to claim 2, wherein the weight ratio of silver to palladium is 0.5:1 to 3:1.

4. A catalyst according to claim 1 wherein:
the palladium content is 0.01% to 0.5% by weight;
the silver content is 0.001% to 0.1% by weight; and
the alumina has a specific surface area of 5 to 15 m$^2$/g.

5. A catalyst according to claim 1 further comprising at least one alkali or alkaline-earth metal.

6. A catalyst according to claim 5, wherein the atomic ratio of alkali or alkaline-earth metal to palladium is 2:1 to 20:1.

7. A catalyst according to claim 6, wherein the alkali or alkaline-earth metal content is 0.05% to 0.2% by weight.

8. The catalyst of claim 1, wherein said catalyst consists essentially of said alumina support and said palladium, silver, and at least one alkali or alkaline earth metal.

9. A catalyst according to claim 1, wherein the weight ratio of silver to palladium is 0.5:1 to 3:1.

10. A catalyst according to claim 5, wherein the weight ratio of silver to palladium is 0.5:1 to 3:1.

11. A catalyst according to claim 1, wherein the weight ratio of silver to palladium is 0.5:1 to 2.5:1.

12. A catalyst in accordance with claim 1, wherein the specific surface is 5 m$^2$/g to 15 m$^2$/g.

13. In a process for selective gas phase hydrogenation of at least one acetylenic hydrocarbon containing 2 or 3 carbon atoms to the corresponding ethylenic hydrocarbon, comprising passing an ethylene feed comprising at least one acetylenic hydrocarbon containing 2 or 3 carbon atoms in the gas phase in the presence of hydrogen over a hydrogenation catalyst in the form of spherules or extrudates, under hydrogenating conditions and wherein the catalyst is deactivated as the hydrogenation proceeds, the improvement comprising decreasing the rate of deactivation by employing a catalyst in accordance with claim 1 as said hydrogenation catalyst.

14. A process according to claim 13, wherein the weight ratio of silver to palladium is 0.5:1 to 3:1.

15. The process of claim 12, wherein the molar ratio of said hydrogen to said acetylenic hydrocarbon is in the range of 1:1 to 2:1.

16. A process according to claim 13, wherein at least 50% of the metallic particles contain both palladium and silver.

17. A process according to claim 13, wherein:
said alumina has a specific surface area of 5 to 60 m$^2$/g;
the palladium content is 0.01% to 0.5% by weight; and
the group IB metal content is 0.001% to 0.1% by weight.

18. A process according to claim 17, wherein the alumina has a specific surface area of 5 to 15 m$^2$/g.

19. A process according to claim 16, characterized in that the catalyst also contains at least one alkali or alkaline-earth metal.

20. A process according to claim 19, wherein the atomic ratio of alkali or alkaline-earth metal to palladium is 2:1 to 20:1.

21. A process according to claim 19, wherein the alkali or alkaline-earth metal content is 0.05% to 0.2% by weight.

22. A process according to claim 13, wherein the alumina in the catalyst has a specific surface area of 5 to 15 m$^2$/g.

23. A process according to claim 22, said catalyst further comprising at least one alkali or alkaline-earth metal.

24. A process according to claim 23, wherein the atomic ratio of alkali or alkaline-earth metal to palladium in the catalyst is 2:1 to 20:1.

25. A process according to claim 23, wherein the alkali or alkaline-earth metal content is in the catalyst 0.05% to 0.2% by weight.

26. A process in accordance with claim 19, wherein the specific surface of the alumina support is 5 m$^2$/g to 15$^2$/g.

27. In a process for selective gas phase hydrogenation of acetylene to the corresponding ethylenic hydrocarbon, comprising passing an ethylene feed, consisting essentially of ethylene and a minor quantity of acetylene as a contaminant, in the gas phase in the presence of hydrogen over a hydrogenation catalyst in the form of spherules or extrudates, under hydrogenating conditions and wherein the catalyst is deactivated as the hydrogenation proceeds, the improvement comprising decreasing the rate of deactivation by employing a catalyst in accordance with claim 1 as said hydrogenation catalyst.

* * * * *